United States Patent [19]

Kleeberg et al.

[11] Patent Number: 4,812,490

[45] Date of Patent: Mar. 14, 1989

[54] EPOXY RESIN MOLDING COMPOUNDS

[75] Inventors: Wolfgang Kleeberg, Erlangen; Heinz Hacker, Nuremberg; Jürgen Huber, Erlangen; Dieter Wilhelm, Forchheim; Heinz K. Laupenmühlen, Hemhofen, all of Fed. Rep. of Germany

[73] Assignee: Siemens Aktiengesellschaft, Berlin and Munich, Fed. Rep. of Germany

[21] Appl. No.: 132,405

[22] Filed: Dec. 14, 1987

[30] Foreign Application Priority Data

Dec. 15, 1986 [DE] Fed. Rep. of Germany ....... 3642782

[51] Int. Cl.$^4$ ............................ C08K 7/04; C08K 3/36
[52] U.S. Cl. .................................... 523/443; 523/466; 528/118; 528/367
[58] Field of Search ................ 523/443, 466; 528/118, 528/367; 525/304

[56] References Cited

U.S. PATENT DOCUMENTS 2,838,511  6/1958  Kogon ................................ 260/248
4,525,534  6/1985  Rasshofer ............................ 528/53

FOREIGN PATENT DOCUMENTS 2743680  4/1979  Fed. Rep. of Germany .
3210746  2/1984  Fed. Rep. of Germany .
3227219  2/1984  Fed. Rep. of Germany .

OTHER PUBLICATIONS

Lee et al., Handbook of Epoxy Resins; McGraw-Hill Book Co.; 1967; pp. 14-2,5,17,49,50.

*Primary Examiner*—Lewis T. Jacobs
*Attorney, Agent, or Firm*—Kenyon & Kenyon

[57] ABSTRACT

Molding compounds for encapsulating semiconductor components comprise filler-containing polyepoxy resins and a 1,3,5-tris(3-amino-4-alkylphenyl)-2,4,6-trioxohexahydrotriazine with a $C_1$ to $C_4$ alkyl radical as a hardener. The molding compounds are storage-stable and moldings manufactured therefrom meet the requirements for these materials.

21 Claims, No Drawings

EPOXY RESIN MOLDING COMPOUNDS

BACKGROUND OF THE INVENTION

The invention relates to molding compounds (i.e., molding materials) for encapsulating semiconductor components. These compounds include an aromatic and/or heterocyclic polyepoxy resin, an aromatic polyamine as a hardener, and mineral fillers in powder form. The mineral fillers may be in a mixture with inorganic short fibers. The invention further relates to moldings (i.e., molded materials) made from such molding compounds.

Cross-linkable (i.e., hardenable) resin systems are of special importance for insulation technology, especially as resin matrices for molding compounds. Examples of such resin systems include epoxy resin molding compounds, especially those in the form of the reaction resin molding compounds Type 870 and Type 871 (see in this connection: H. Saechtling, "Kunststoff-Taschenbuch", 20th Edition, 1977, page 416 and Table 85), that is epoxy resin molding compounds (according to DIN 16912) with an inorganic granular or inorganic short-fiber filler.

While the epoxy resin molding compounds, especially those with aminic hardeners of the aromatic amine type such as 4,4'-diaminodiphenyl-sulfone (see, for instance, DE-OS No. 32 10 746) furnish high quality moldings in the cross-linked state, they have only limited storage stability. These molding compounds do not permit adjustment of a state with stationary properties, due to the continuously progressing reaction between the epoxy resin and the amine which progresses rapidly even at low temperatures. Furthermore, the continuously progressing chemical reaction between the epoxy group and the amine hydrogen causes a corresponding change of the processing parameters and may also influence the quality of the moldings produced from the molding compounds.

Molded materials with high dimensional stability under heat can be made from polyepoxy resins (i.e., polyglycidyl compounds) and polyamines with isocyanurate structure elements, such as known from German Pat. No. 27 43 680. However, it is apparent that there is a problem of limited processability with respect to such molding compounds.

It is, therefore, an object of the invention to develop storage stable molding compounds for encapsulating semiconductor components which compounds include a polyepoxy resin and a polyamine as a hardener. It is a further object of the invention to develop storage molding compounds which ensure that moldings manufactured therefrom meet the requirements desired of these materials.

SUMMARY OF INVENTION

The invention is a molding compound for encapsulating semiconductor components comprising a filler-containing polyepoxy resin and a polyamine as a hardener. The hardener is a 1,3,5-tris(3-amino-4-alkylphenyl)-2,4,6-trioxo-hexahydrotriazine with a $C_1$ to $C_4$ alkyl radical, i.e., an isocyanuric acid derivative. The invention also relates to epoxy resin moldings made from such molding compounds.

DETAILED DESCRIPTION

The compounds used as the hardener in the molding compounds according to the invention are primary polyamines containing aromatic amino groups. Such polyamines can be made, for example, by hydrolysis of suitable compounds with free isocyanate groups. A method of this kind is known, for instance, from DE-OS No. 32 27 219. The polyamines made by the known method serve for the manufacture of polyurethanes, polyurethane plastics and polyurethane foam materials. Although DE-OS No. 32 27 219 states that one possible application of the polyamines (among other applications) is as a "hardener for epoxy and phenolic resins", it is entirely surprising and could in no way be foreseen that, of the large number of compounds mentioned in the patent, just one special polyamine type, namely, 1,3,5-tris(3-amino-4-alkylphenyl)-2,4,6-trioxo-hexahydrotriazine could be used as the hardener in filler-containing epoxy resin molding compounds for encapsulating semiconductor components and that molding compounds made with this hardener have great storage stability and lead to epoxy resin molded materials with a high quality level.

The hardener used in the molding compounds according to the invention is prepared from 2,4-diisocyanato-alkylbenzenes such as 2,4-diisocyanatotoluene. The diisocyanato-alkylbenzenes (alkyl=$CH_3$, $C_2H_5$, $C_3H_7$ or $C_4H_9$) are trimerized by means of suitable catalysts and converted into 1,3,5-tris(3-isocyanato-4-alkylphenyl)-2,4,6-trioxo-hexahydrotriazines. The polyamines are then formed therefrom by hydrolysis of the isocyanate groups.

If non-reacted starting material (i.e., monomeric diisocyanato alkyl benzene) is present in the reaction mixture obtained in the trimerization, aromatic polyamines are formed in the hydrolysis as a byproduct. Such polyamines can be employed as an additive hardener component in the molding compounds according to the invention, besides the hardener proper.

In the hydrolysis of the trimerization product containing isocyanate groups a reaction between isocyanate groups and amino groups can also occur. Hereby, heterocyclic polyamines with urea groupings are obtained as a byproduct of the hydrolysis reaction. Such polyamines can also be employed in the molding compounds according to the invention as an additive hardener component, i.e., in a mixture with the hardener proper.

Preferably, in the molding compounds according to the invention, hydrolysis products of trimerized diisocyanato alkyl benzenes are used as hardeners, i.e., hardener mixtures. In hardener mixtures of this kind, the content of the hardener proper (i.e., 1,3,5-tris(3-amino-4-alkylphenyl)-2,4,6-trioxo-hexahydrotriazine) in the mixture is advantageously at least 50% by weight and preferably between 80 and 95% by weight. The ratio of the epoxy function used to the amine hydrogen function (NH) used is otherwise advantageously about 0.9:1 to about 1.1:1, and preferably about 1:1.

Besides the hardener proper or besides hardener mixtures of the type mentioned above, aromatic polyamines of a different type can be used in the molding compounds according to the invention. Such aromatic polyamines include 4,4'-diaminodiphenylmethane and 4,4'-diaminodiphenylsulfone. Other heterocyclic polyamines may also be used. The content of such polyamines in the hardener mixture is maximally 5% by weight.

Suitable polyepoxides (i.e., polyglycidyl compounds with at least two epoxy groups per molecule) include epoxized (i.e., epoxidized) novolaks, polyglycidyl ethers with a bisphenol A, bisphenol F or bisphenol B base as well as epoxized hydantoines and triglycidyl isocyanurate. The epoxides can also be present as a mixture. Preferably, the polyepoxy resin is an epoxized novolak with an epoxy number of 0.3 to 0.6 and a total content of hydrolyzable halogen of less than 0.6% by weight, and preferably less than 0.1% by weight. Advantageously, the epoxized novolak can be used together with triglycidylisocyanurate.

The polyepoxy resin can also be a mixture of an epoxized novolak and nucleus-halogenated bisphenol-bisglycidyl ether and/or a nucleus-halogenated epoxized novolak, the total content of the mixture of nucleus-bound halogen being maximally 4% by weight. From molding compounds of the last mentioned type (i.e., halogen containing molding compounds) epoxy resin molded materials with further improved flame retarding properties are obtained. For, such molding compounds reach the flame-retarding property of the stage UL 94 V-0.

According to the invention, mineral fillers in powder form are used in the molding compounds. These mineral fillers can also be used in a mixture with inorganic short fibers in the form of milled glass fibers. Milled glass fibers have a fiber length of less than 1 mm, in accordance with DIN 61850; the mean fiber length is preferably about 0.2 mm. Mineral fillers which can be used with or without an adhesion agent include carbonates such as dolomite, in the form of Microdol ®, as well as aluminum oxides and aluminum oxide hydrates. Preferably, low-alpha radiation meals of quartz or fused quartz, especially of low-alpha radiation raw materials such as rock crystal serve as fillers, or silicon dioxide ($SiO_2$) with low-alpha activity, as is known from DE-OS No. 33 23 844. Silicon dioxide of this kind is free of impurities like thorium and uranium which are responsible for the alpha emission; it therefore has emission rates of less than 0.01 alpha particles/$cm^2$/hr.

The filler content in the molding compounds according to the invention is generally between 50 to 85% by weight; preferably, this content is 70 to 80% by weight. If the filler contains milled-glass fibers in addition to mineral materials in powder form, then the fiber content in the filler mixture should be from 3 to 40% by weight. Examples of fiber-like fillers with a mineral base which can be used include calcium silicates such as Wollastonite.

The molding compounds according to the invention can be processed in such a way that polyepoxy resin, polyamine (hardener) and filler are mixed directly with each other in suitable mixing devices for instance, in a roller frame (so-called by dry processing). Alternatively, the fillers can be placed in a solution of polyepoxy resin and hardener in a suitable organic solvent (so-called wet processing). Suitable wet processing solvents include acetone, ethylacetate, methylethylketone and methylglycol(2-methoxyethanol). Acetone and other ketonic solvents are preferred. The wet processing solutions have a content of 40 to 60% by weight (preferably about 50% by weight) polyepoxy resin and hardener. After adding the fillers and mixing, the solvent is removed from the solutions in a vacuum, for instance, at a pressure of 1 mbar and a temperature of 60° C.

In general, the molding compounds according to the invention are processed by customarily transfer molding methods, i.e., they are pressed under elevated pressure and at elevated temperature. At temperatures above 150° C., the molding compounds according to the invention are then converted into the corresponding moldings in a fast cross-linking reaction.

The epoxy resin molding compounds according to the invention have great storage stability. Storage stability is attributed to the fact that the polyaddition reaction is delayed at room temperature to such an extent that perfect processability is retained over a period of at least 12 weeks at room temperature. At temperatures above 150° C., however, rapid cross-linking takes place. The molding compounds of the invention are further distinguished by a low reaction shrinkage (less than 6%).

Moldings made from the molding compounds of the invention have a high glass transition temperature ($T_g$ more than 200° C.) and a low linear thermal expansion coefficient in the temperature range from room temperature to about 210° C. The molding compounds have a thermal expansion coefficient in the range of 15 to $25 \times 10^{-6}$ $K^{-1}$, depending on the filler type and content. Because the α-jump is missing (i.e., the thermal linear expansion coefficient in the glass transition range is changing) reduced stresses are exerted on the overall system in the range of application.

The molded materials according to the invention are also self-extinguishing. With an average burning time of 5 seconds (without the addition of halogen) they are considered, according to IEC 249-1, difficult to burn.

The molded materials further exhibit good adhesion to metals, which is important for the encapsulation of semiconductor components. The tightness of the pins against the penetration of moisture is assured.

The invention will be explained in further detail, referring to embodiment examples.

EXAMPLE 1

Preparation of
1,3,5-tris(3-isocyanato-4-methylphenyl)-2,4,6-trioxohexahydrotriazine 500 g 2,4-diisocyanato toluene (NCO content: 48.2%) are trimerized with sodium benzoate dissolved in dimethylformamide (see, in this connection, U.S. Pat. No. 2,801,244). After about 1 hour, the reaction is stopped at an NCO value of 24.8% by adding p-toluene sulfonic acid.

EXAMPLE 2

Preparation of
1,3,5-tris(3-amino-4-methylphenyl)-2,4,6-trioxo-hexahydrotriazine The hydrolysis of isocyanate compounds into the corresponding amines is described sufficiently in the literature. Examples for hydrolysis by means of basic and acid catalysts can be found in French Pat. No. 14 15 317, DE-AS No. 11 55 907, DE-OS No. 29 48 419, DE-OS No. 30 39 600, DE-OS No. 31 12 118, DE-OS No. 32 44 912 and DE-OS No. 32 44 913. Another possibility of amine synthesis is based on the thermal decomposition of addition products of isocyanates and alcohol such as is described, for instance, in DE-AS No. 12 70 046 and DE-OS No. 30 35 639. The hydrolysis of isocyanate compounds proceeds particularly well with concentrated sulfuric acid (corresponding to German Pat. No. 27 43 680) or in high-boiling solvents (corresponding to DE-OS No. 32 27 219).

In the hydrolysis of 1,3,5-tris(3-isocyanato-4-methylphenyl)-2,4,6-trioxo-hexahydrotriazine according to DE-OS No. 32 27 219 a solution of the timerisate prepared according to EXAMPLE 1 in dimethylacetamide is added to a hot mixture of dimethylacetamide, water and Florisil, as a catalyst (Florisil ®, a product of Floridin Corp., consists substantially of magnesium silicate). After the processing, a mixture of 1,3,5-tris(3-amino-4-methylphenyl)-2,4,6-trioxo-hexahydrotriazine and heterocyclic polyamines with an $NH_2$ content of 6.8% by weight is obtained.

EXAMPLE 3

Preparation of Molding Compounds (a) Processing in a solvent (wet processing)

450 parts by weight of an epoxized novolak with an epoxy value of 0.57 are dissolved in 450 parts by weight acetone. To this solution is added a solution of 300 parts by weight of the hardener mixture prepared in accordance with EXAMPLE 2 ($NH_2$ content: 6.8% by weight) in 300 parts by weight acetone. The 50-percent resin/hardener solution obtained in this manner is reacted with 1630 parts by weight quartz meal, for instance, in the form of Silbond ® of Quarzwerke GmbH, and mixed. The mixture is then poured on an aluminum foil and the solvent is removed in a vacuum drying cabinet (pressure: 1 mbar; temperature: 60° C.; time: 30 min.). The pourable mass obtained in this manner is storage-stable for 6 months at 5° C. and 3 months at room temperature.

(b) Dry Processing 600 parts by weight of an epoxized novolak with an epoxy value of 0.57 are mixed together with 400 parts by weight of the hardener mixture prepared in accordance with EXAMPLE 2 ($NH_2$ content: 6.8% by weight) and 2170 parts by weight quartz meal (for instance, in the form of Silbond ®) on a roller frame for 30 minutes (roller temperature: 60° C. ). In the process a pourable mass fluid is obtained which is storage stable for more than 3 months at room temperature and more than 6 months at 5° C.

EXAMPLE 4

Preparation of Molded Materials in the Form of Test Specimens

Storage-stable molding compounds according to EXAMPLE 3 are processed by the customary transfer molding methods into test specimens (molding temperature: 175° C.; molding pressure 100 bar; molding time: 5 min.). Measurement of the thermomechanical properties at the test specimens which was made by the customary DIN methods furnished the following results:

| glass transition temperature Tg: (according to DIN 53445) | |
| --- | --- |
| without anneal | 210° C. |
| annealed for 2 hrs. at 190° | 220° C. |
| annealed for 2 hrs. at 210° C. | 233° C. |
| annealed for 2 hrs. at 220° C. | 240° C. |
| bending stress: wet processing (according to DIN 53 452) | |
| unannealed | annealeded* |
| 168 ± 17 N/mm² | 134 ± 30 N/mm² |
| dry processing | annealed* |
| | 162 ± 18 N/mm² |
| impact resistance wet processing (according to DIN 53 453) | |
| unannealed | annealed* |
| 5.7 ± 1.4 Nmm/mm² | 6.2 ± 1.0 Nmm/mm² |
| dry processing | annealed* |
| | 6.1 ± 1.1 Nmm/mm² |

*up to 220° C.

What is claimed is:

1. A molding compound for encapsulating semiconductor components comprising: an aromatic and/or heterocyclic polyepoxy resin; 1,3,5-tris(3-amino-4-alkylphenyl)-2,4,6-trioxo-hexahydrotriazine with a $C_1$ to $C_4$ alkyl radical as a hardener; and a mineral filler in powder form.

2. A molding compound according to claim 1 in which the mineral filler is in a mixture with inorganic short fibers.

3. A molding compound according to claim 1 in which the hardener is present in a mixture with aromatic and/or heterocyclic polymines.

4. A molding compound according to claim 3 in which the content of 1,3,5-tris(3-amino-4-alkylphenyl)-2,4,6-trioxo-hexahydrotriazine in the hardener mixture is at least about 50% by weight.

5. A molding compound according to claim 4 in which the content of 1,3,5-tris(3-amino-4-alkylphenyl)-2,4,6-trioxo-hexahydrotriazine in the hardener mixture is between about 80 and about 95% by weight.

6. A molding compound according to claim 1 in which the ratio of epoxy groups to amine hydrogen is from about 0.9:1 to about 1.1:1.

7. A molding compound according to claim 1 in which the polyepoxy resin is an epoxized novolak with an epoxy number of about 0.3 to about 0.6 and a total content of hydrolyzable halogen which is less than about 0.6% by weight.

8. A molding compound according to claim 1 in which the filler is selected from the group consisting of quartz meal, fused quartz meal and synthetically made silicon dioxide with an emission rate of less than about 0.01 alpha particles/cm²/hr.

9. A molding compound according to claim 1 in which the filler content is between about 50 to about 85% by weight relative to the total weight of the compound.

10. A molding compound for encapsulating semiconductor components comprising: an epoxized novolak with an epoxy number of about 0.3 to about 0.6 and a total content of hydrolyzable halogen which is less than about 0.6% by weight; a hardener mixture comprised of 1,3,5-tris(3-amino-4-alkylphenyl)-2,4,6-trioxo-hexahydrotriazine with a $C_1$ to $C_4$ alkyl radical and other aromatic or heterocyclic polyamines or mixtures thereof in which the content of the hexahydrotriazine in the hardener mixture is at least about 50% by weight; and one or more mineral fillers selected from the group consisting of quartz meal, fused quartz meal and synthetically made silicon dioxide with an alpha emission rate of less than about 0.01 alpha particles/cm²/hr.

11. A molding compound according to claim 10 in which the mineral fillers are in a mixture with inorganic short fibers.

12. A molding compound according to claim 10 in which the ratio of epoxy to amine hydrogen function is from about 0.9:1 to about 1.1:1.

13. A molding compound according to claim 10 in which the polyepoxy resin is a mixture of an epoxized novolak and triglycidyl isocyanurate.

14. A molding compound according to claim 10 in which the polyepoxy resin is a mixture of epoxized novolak and a nucleus-halogenated bisphenol bisglycidyl ether or a nucleus-brominated epoxized novolak or a mixture thereof, wherein the total content of the mixture of nucleus-bound halogen is equal to or smaller than about 4% by weight relative to the total weight of the resin.

15. A molding compound according to claim 10 in which the filler content is between about 50 to about 85% by weight.

16. A molding compound for encapsulating semiconductor components comprising: an aromatic and/or heterocyclic polyepoxy resin which is a mixture of triglycidyl isocyanurate and an epoxized novolak with an epoxy number of about 0.3 to about 0.6 and a total content of hydrolyzable halogen which is less than about 0.6% by weight; 1,3,5-tris(3-amino-4-alkylphenyl)-2,4,6-trioxo-hexahydrotriazine with a $C_1$ to $C_4$ alkyl radical as a hardener; and a mineral filler in powder form.

17. A molding compound for encapsulating semiconductor components comprising: an aromatic and/or heterocyclic polyepoxy resin which is a mixture of an epoxized novolak with an epoxy number of about 0.3 to about 0.6 and a total content of hydrolyzable halogen which is less than about 0.6% by weight and a nucleus-halogenated bisphenol bisglycidyl ether or a nucleus-brominated epoxized novolak or mixture thereof, wherein the total content of the mixture of nucleus bound halogen is equal to or smaller than about 4% by weight relative to the total weight of the resin; 1,3,5-tris(3-amino-4-alkylphenyl)-2,4,6-trioxo-hexahydrotriazine with a $C_1$ to $C_4$ alkyl radical as a hardener; and a mineral filler in powder form.

18. A molding compound according to claim 16 in which the hardener is present in a mixture with aromatic and/or heterocyclic polyamines in which the content of 1,3,5-tris(3-amino-4-alkylphenyl)-2,4,6-trioxo-hexahydrotriazine in the hardener mixture is at least about 50% by weight.

19. A molding compound according to claim 17 in which the hardener is present in a mixture with aromatic and/or heterocyclic polyamines in which the content of 1,3,5-tris(3-amino-4-alkylphenyl)-2,4,6-trioxo-hexahydrotriazine in the hardener mixture is at least about 50% by weight.

20. A molding compound according to claim 16 in which the ratio of epoxy groups to amine hydrogen is from about 0.9:1 to about 1.1:1.

21. A molding compound according to claim 17 in which the ratio of epoxy groups to amine hydrogen is from about 0.9:1 to about 1.1:1.

* * * * *